United States Patent [19]
Zapol et al.

[11] Patent Number: 5,904,938
[45] Date of Patent: May 18, 1999

[54] TREATMENT OF VASCULAR THROMBOSIS AND RESTENOSIS WITH INHALED NITRIC OXIDE

[75] Inventors: Warren M. Zapol, Concord; Kenneth D. Bloch, Brookline, both of Mass.

[73] Assignee: The General Hospital Corporation, Boston, Mass.

[21] Appl. No.: 08/785,529

[22] Filed: Jan. 17, 1997

Related U.S. Application Data

[62] Division of application No. 08/389,304, Feb. 16, 1995.

[51] Int. Cl.$^6$ .................................................. A61K 33/00
[52] U.S. Cl. ............................................ 424/718; 514/822
[58] Field of Search ........................... 424/718; 435/215, 435/216, 359; 514/56, 165, 822

[56] References Cited

U.S. PATENT DOCUMENTS

| | | | |
|---|---|---|---|
| 3,785,377 | 1/1974 | Jorgensen | 128/188 |
| 4,010,897 | 3/1977 | Treharne et al. | 239/8 |
| 4,287,040 | 9/1981 | Alamaro | 204/179 |
| 4,297,123 | 10/1981 | Wyse et al. | |
| 4,336,798 | 6/1982 | Beran | |
| 4,534,343 | 8/1985 | Nowacki et al. | |
| 4,592,348 | 6/1986 | Waters et al. | |
| 4,667,668 | 5/1987 | Wetterlin | |
| 4,852,561 | 8/1989 | Sperry | |
| 4,877,589 | 10/1989 | O'Hare | 422/186.24 |
| 4,915,915 | 4/1990 | Treharne et al. | 422/186.24 |
| 4,954,526 | 9/1990 | Keefer et al. | 514/611 |
| 5,155,137 | 10/1992 | Keefer et al. | 514/611 |
| 5,185,376 | 2/1993 | Diodati et al. | 514/611 |
| 5,208,233 | 5/1993 | Keefer et al. | 514/231.8 |
| 5,385,937 | 1/1995 | Stamler et al. | 514/557 |
| 5,396,882 | 3/1995 | Zapol | |
| 5,427,797 | 6/1995 | Frostell et al. | 424/434 |
| 5,570,683 | 11/1996 | Zapol | 128/200.14 |
| 5,681,278 | 10/1997 | Igo et al. | 604/52 |

FOREIGN PATENT DOCUMENTS

| | | |
|---|---|---|
| 0 589 751 A1 | 3/1994 | European Pat. Off. |
| 43 27 732 C1 | 9/1994 | Germany |
| 43 27 731 C1 | 11/1994 | Germany |
| A-2 144 997 | 3/1985 | United Kingdom |
| WO 93/177411 | 3/1992 | WIPO |
| WO 92/10228 | 6/1992 | WIPO ........................... A61M 11/00 |
| WO 92/17445 | 10/1992 | WIPO |
| WO 92/18002 | 10/1992 | WIPO ........................... A01N 37/12 |
| WO 93/12068 | 6/1993 | WIPO |
| WO 94/00180 | 1/1994 | WIPO ........................... A61M 31/00 |
| WO 94/16729 | 8/1994 | WIPO ........................... A61K 39/395 |
| WO 94/22499 | 10/1994 | WIPO ........................... A61L 9/04 |
| WO95/02181 | 1/1995 | WIPO |

OTHER PUBLICATIONS

Allen and Hanbury, Product Information Bulletin on Ventolin, (1990).
Zapol, U.S. Ser. No. 07/622,865, Dec. 5, 1990.
Zapol, U.S. Ser. No. 07/767,234, Sep. 27, 1991.
Zapol, U.S. Ser. No. 07/904,117, Jun. 25, 1992.
Zapol, U.S. Ser. No. 08/036,522, Mar. 24, 1993.
Zapol, et al., U.S. Ser. No. 08/353,508, Dec. 9, 1994.
Zapol, U.S. Ser. No. 07/850,383, Mar. 11, 1992.
Zapol, U.S. Ser. No. 08/222,256, Apr. 1, 1994.

(List continued on next page.)

*Primary Examiner*—Robert H. Harrison
*Attorney, Agent, or Firm*—Fish & Richardson P.C.

[57] ABSTRACT

Disclosed are methods of treating, inhibiting or preventing vascular thrombosis or arterial restenosis in a mammal. The disclosed methods include causing the mammal to inhale a therapeutically-effective concentration of gaseous nitric oxide (NO). Also disclosed are methods that include the administration of the following types of agents in conjunction with inhaled nitric oxide: compounds that potentiate the beneficial effects of inhaled nitric oxide, and antithrombotic agents that complement or supplement the beneficial effects of inhaled nitric oxide.

24 Claims, 5 Drawing Sheets

OTHER PUBLICATIONS

Altabef et al., Intravenous Nitroglycerin for Uterine Relaxation of an Inverted Uterus, *Am. J. Obstet. Gynecol.* 166:1237–1238, (1992).

Änngård, "Nitric Oxide: Mediator, Murderer, and Medicine," *Lancet,* 343:1199–1205 (1994).

Archer, et al., "Hypoxic Pulmonary Vasoconstriction is Enhanced by Inhibition of the Synthesis of an Endothelium Relaxing Derived Factor," *Biochem. Biophys. Res. Commun.* 164:1198–1205 (1989).

Archer, et al., "Comparison of the Hemodynamic Effects of Nitric Oxide and Endothelium–Dependent Vasodilators in Intact Lungs," *J. App. Physiol.* 68:735–747 (1990).

Arnold, et al., "Cigarette–Smoke Activates Guanylate Cyclase and Increase Guanosine 3', 5' –Monophosphate in Tissues", *Science,* 198:934–936 (1977).

"Asthma", Ch. 14–II, *Scientific American Medicine,* vol. 2, Scientific American, Inc., pp. 1–18 (1988).

Benzing et al., "Nitric Oxide Inhalation. Application and Continuous Measurment of Inhaled Concentration," *Anaesthesist* (1993) 42:175–178 (Abstract in English).

Blomqvist, et al., "Inhaled Nitric Oxide (NO): A Selective Pulmonary Vasodilator Reversing Human Hypoxic Pulmonary Vasoconstriction (HPV)," *Circulation* 84:361 (1991).

Boje, et al., "Endothelial Nitric Oxide Generating Enzyme(s) in the Bovine Aorta: Subcellular Location and Metabolic Characterization," *Am. Soc. Pharmacol. Exp. Ther.* 253:20–26 (1990).

Borland, et al., "A Simultaneous Single Breath Measurement of Pulmonary Diffusing Capacity with Nitric Oxide and Carbon Monoxide," *Eur. Respir. J.* 2:56–63 (1989).

Brashers, et al., "Augmentation of Hypoxic Pulmonary Vasoconstriction in the Isolated Perfused Rat Lung by in Vitro Antagonists of Endothelium–Dependent Relaxation," *J. Clin. Invest.* 82:1495–1502 (1988).

Brune, et al., "Activation of a Cystolic ADP–Ribosyltransferase by Nitric Oxide–Generating Agents," *J. Biol. Chem.* 264:8455–8458 (1989).

Buga, et al., "Endothelium–Derived Nitric Oxide Relaxes Nonvascular Smooth Muscle," *Eur. J. Pharmacol.* 161:61–72 (1989).

Contractor, et al., "Development and Evaluation of an Inhalation Aerosol of Nitroglycerin," *J. Pharm. Sci.* 63:907–911 (1974).

Cremona, et al., "Endothelium–Derived Relaxing Factor and the Pulmonary Circulation," *Lung* 169:185–202 (1991).

Curran, et al., "Nitric Oxide and Nitric Oxide–Generating Compounds Inhibit Hepatocyte Protein Synthesis," *FASEB J.* 5:2085–2092 (1991).

Dalby, et al., "Comparison of Output Particle Size Distributions from Pressurized Aerosols Formulated as Solutions or Suspensions," *Pharmacol. Res.* 5:36–39 (1988).

Desai, et al., "Involvement of Nitric Oxide in the Reflex Relaxation of the Stomach to Accommodate Food or Fluid," *Nature* 351:477 (1991).

Dihn Xuan, et al., "Acetylcholine and Adenosine Diphosphate Cause Endothelium–Dependent Relaxation of Isolated Human Pulmonary Arteries," *Eur. Respir. J.,* 3:633–638 (1990).

Dihh Xuan, et al., "Primary Pulmonary Hypertension: Diagnosis, Medical and Surgical Treatment," *Resp. Med.,* 84:189–197 (1990).

Dihn Xuan, et al., "Non–prostanoid Endothelium–Derived Vasoactive Factors," *J. Intl. Med. Res.* 17:305–315 (1989).

Donahue, et al., "Production of $O_3$, NO, and $N_2O$ in a Pulsed Discharge at 1 Atm," *Ind. Eng. Chem.,* 16:208–215 (1977).

Dupuy, et al., "Bronchodilator Action of Inhaled Nitric Oxide in Guinea Pigs," *J. Clin. Invest.* 90:421–428 (1992).

Dworetz, et al., "Survival of Infants with Persistent Pulmonary Hypertension without Extracorporeal Membrane Oxygenation," *Pediatrics,* 84:1–6 (1989).

Edwards, et al., "Activation of Hepatic Guanylate Cyclase by Nitrosyl–Heme Complexes," *Biomed. Pharmacol.* 30:2531–2538 (1981).

Fishman, "Pulmonary Hypertension and Cor Pulmonate," *Pulmonary Diseases and Disorders, 2nd Ed.,* vol. 2 McGraw–Hill, New York, Chapter 64, pp. 999–1048.

Flavahan, et al., "Respiratory Epithelium Inhibits Bronchial Smooth Muscle Tone," *J. Appl. Physiol.* 58:834–838 (1985).

Flentley, "Today's Treatment of Airway Obstruction . . . and Tomorrow's?", *Respiration* 55:4–9 (1989).

Foubert, et al., "Safety Guidelines for Use of Nitric Oxide," *Lancet* 339:1616 (1992).

Fox, et al., "Pulmonary Hypertension in the Perinatal Aspiration Syndromes," *Pediatrics* 59:205–211 (1977).

Fratacci, et al., "Inhaled Nitric Oxide: A Selective Pulmonary Vasodilator of Heparin–Protamine Vasoconstriction in Sheep," *Anesthesiology* 75:990–999 (1991).

Frostell, et al., "Inhaled Nitric Oxide: A Selective Pulmonary Vasodilator Reversing Hypoxic Pulmonary Vasoconstriction," *Circulation* 83:2038–2047 (1991).

Frostell et al., "Inhaled Nitric Oxide Selectively Reverses Human Hypoxic Pulmonary Vasoconstriction Without Causing Systemic Vasodilation," *Anesthesiology* 78:427–35 (1993).

Furchgott, et al., "Endothelium–Derived Relaxing and Contracting Factors," *FASEB J.* 3:2007–2018 (1989).

Garg, et al., "Nitric Oxide Generating Vasodilators Inhibit Mitogenesis and Proliferation of BALB/C 3T3 Fibroblasts by a Cyclic GMP–Independent Mechanism," *Biochem. Biophys. Res. Commun.* 171:474–479 (1990).

Garg, et al., "Nitric Oxide Generating Vasodilators and 8–Bromo–Cyclic Guanosine Monophosphate Inhibit . . . Vascular Smooth Muscle Cells," *J. Clin. Invest.* 83:1774–1777 (1989).

Gilman, et al., "Vascular Effects of Cigarette Smoke in Isolated Pig Lungs," *Am. Rev. Respir. Dis.* 124:549–553 (1981).

Gold, et al., "Animal Models for Arterial Thrombolysis and Prevention of Reooculsions," *Circulation,* 83:26–40 (1991).

Groves, et al., "SIN–1 Reduces Platelet Adhesion and Platelet Thrombus Formation in a Porcine Model of Balloon Angioplasty," *Circulation* 87:590–597 (1993).

Heaslip, et al., "Co–Regulation of Tracheal Tone by Cyclic AMP– and Cyclic GMP–Dependent Mechanisms," *J. Pharmacol. Exp. Ther.,* 243:1018–1026 (1987).

Higgenbottam, et al.,"Inhaled Endothelium Derived–Relating Factor (EDDIF) in Primary Hypertension (PPH)," *Am. Rev. Resp. Dis. Suppl.* 137:107, (1988).

Högman, et al., "Prolonged Bleeding Time During Nitric Oxide Inhalation in the Rabbit," *Acta. Physiol.Scand.* 151:125–129 (1994).

Högman, et al., "Bleeding Time Prolongation and NO Inhalation," *Lancet,* 341:1664–1665 (1993); Abstract.

Hounam, et al., "Particle Depositions", *Respiratory Defense Mechanisms,* Part 1, pp. 125–156 (1977).

Hugod, "Effect of Exposure to 43 ppm Nitric Oxide and 3.6 ppm Nitrogen Dioxide on Rabbig Lung," *Int. Arch. Occup. Environ. Health* 42:159–167 (1979).

Ichinose, et al., "Prolonged Duration of Action of Inhaled Nitric Oxide by Zaprinast, A cGMP Phosphodiesterase Inhibitor, in Awake Lambs," *Am. J. Resp, Critical Care Med.* 149:A22 (1994).

Ignarro, et al., "Endothelium–Derived Relaxing Factor Produced and Released from Artery and Vein is Nitric Oxide," *Proc. Natl. Acad. Sci. USA*, 84:9265–9269 (1987).

Ignarro, "Biosynthesis and Metabolism of Endothelium–Derived Nitric Oxide," *Ann. Rev. Pharmacol. Toxicol.* 30:535–560 (1990).

Ignarro, "Endothelium–Derived Nitric Oxide: Actions and Properties," *FASEB J.* 3:31–36 (1989).

Ignarro, "Biological Actions and Properties of Endothelium–Derived Nitric Oxide Formed and Released From Artery and Vein," *Circ. Res.* 65:1–21 (1989).

Ignarro, et al., "Mechanism of Vascular Smooth Muscle Relaxation by Organic Nitrates, Nitrites, Nitroprusside and Nitric Oxide . . . as Active Intermediates," *J. Pharmacol. Experm. Ther.*, 218:739–749 (1981).

Ishii, et al., "A Simple and Sensitive Bioassay Method for Detection of EDRF with RFL–6 Rat Lung Fibroblasts," *Am. J. Physiol.*, 261:H598–H603 (1991).

Jansen, "The Relaxant Properties in Guinea Pig Airways of S–Nitrosothiois," *J. Pharmacol. Exp. Ther.*, 261:154–160 (1992).

Kacmarek, et al., "Nitric Oxide as a Bronchodilator in Methacholine Induced Bronchospasm in Mild Asthmatics" 1993 ALA/ATS International Conference, May 16–19, 1993, San Francisco, CA #21556 (Abstract).

Kadowitz, et al., "Pulmonary Vasodilator Responses to Nitroprusside and Nitroglycerin in the Dog," *Clin. Invest.*, 67:893–902 (1981).

Kolata, The New York Times, Jul. 2, 1991 p. C1.

Kreye, et al., "Comparison of Sodium Nitropursside and Isoprenaline Aerosols," *Naunyn–Schmiedeberg S Arch Pharmacol.* 306:203–207 (1979).

Kurrek, et al., Inhaled Nitric Oxide Does Not Alter Endotoxin–Induced Nitric Oxide Synthase Activity During Perfusion of the Isolated Rat Lung,: 81:(supplement) Abstract No. 639 (1994).

Mahon, "Drugs and the Respiratory System," in *Principles of Medical Pharmacology, 5th Ed,* (Kalamt et al., ed.) B. C. Decker, pp. 392–397 (1989).

Mang et al., "Gefahren und Möglichkeiten der Therapie mit inhaliertem Stickstoffmonoxid," *Intensivmed* 29:107–113 (1992) (Summary in English).

Maron, et al., "Cigarette Smoke Causes Acute Fluctuations in the Cyclic GMP Content of the Isolated Intact Lung," *Respiration* 44:39–44 (1984).

McNamara, et al., "L–Arginine Inhibits Balloon Catheter––Induced Intimal Hyperplasia," *Biochem. Biophys. Res. Commun.,* 193:291–296 (1993).

McNamara, et al., "Adenosine 3', 5' Monophosphate Formation by Preparations of Rat Liver Soluble Guanylate Cyclase . . . and Other Nitroso Compounds," *Can. J. Physiol. Pharmacol.* 58:1446–1456 (1980).

Meier, "Using Asthma Inhalers, But Correctly," *The New York Times,* Aug. 10, 1991, p. 48.

Messent, et al., "The Pulmonary Physician and Critical Care," *Thorax* 47:651–656 (1992).

Meyer, et al., "Nitric Oxide (NO), a New Test Gas for Study of Alevolar–Capillary Diffusion," *Eur. Respir. J.* 2:494–496 (1989).

Moncada, et al., "Nitric Oxide: Physiology, Pathophysiology, and Pharmacology," *Pharmacl. Rev* 91:109–141 (1991).

Morel, et al., "Acute Pulmonary Vasoconstriction and Thromboxane Release During Protamine Reversal of Heparin Anticoagulation in Awake Sheep," *Circ. Res.* 62:905–915 (1988).

Morel, et al., "C5α and Thromboxane Generation Associated with Pulmonary Vaso–and Broncho Constriction during Protamine Reversal of Heparin," *Anesthesiology* 66:597–604 (1987).

Myers, et al., "Vasorelaxant Properties of the Endothelium–Derived Relaxing Factor More Closely Resemble S–nitrosocysteine than Nitric Oxide," *Nature* 345:161–163 (1990).

Naeije, et al., "Effects of Vasodilators on Hypoxic Pulmonary Vasoconstriction in Normal Man," *Chest* 82:404–410 (1982).

Nakajima, et al., "Biological Effects of Nitrogen Dioxide and Nitric Oxide," *Nitrogen Oxides,* 121–141.

Norman and Keith, "Nitrogen Oxides in Tobacco Smoke," *Nature,* 205:915–916 (1965).

Packer, "Is it Ethical to Administer Vasodilator Drugs to Patients with Primary Pulmonary Hypertension," *Chest* 95:1173–1175 (1989).

Palmer, et al., "Nitric Oxide Release Accounts for the Biological Activity of Endothelium–Derived Relaxing Factor," *Nature,* 327:524–526 (1987).

Peckham, "Physiologic Factors Affecting Pulmonary Artery Pressure in Infants with Persistent Pulmonary Hypertension," *J. Ped.* 6:1005–1010 (1978).

Peppke–Zaba, et al., "Inhaled Nitric Oxide as a Cause of Selective Pulmonary Vasodilation in Pulmonary Hypertension," *Lancet,* 338:1173–1174 (1991).

Radermacher, et al., "Comparison of Ketanserin and Sodium Nitroprusside in Patients with Severe ARDS," *Anesthesiology,* 68:152–157 (1988).

Resnick, et al., "Evaluation and Medical Management of Urinary Incontinence," in *Campbell's Urology, 6th Ed.,* W.B. Saunders, Philadelphia, pp. 652–655.

Rimar, et al., "Prolonged Duration of Inhaled Nitric Oxide Induced Vasodilation in Perfused Rabbit Lungs," *Circulation,* 84:362 (1991).

Kaplan et al., "Roles of Thrombin and Platelet Membrane Glycoprotein IIb/IIIa in Platelet–Subendothelial Deposition After Angioplasty in an Ex Vivo Whole Artery Model," *Circulation* 84:1279 (1991).

Samama, et al., "Platelet Aggregation, Von Willebrand Factor Antigen and Activity, and Inhaled Nitric Oxide (NO) in ARDS Patients," *Brit. J. Anaesthesia* 72 (Supplement 1):110 (1994); Abstract.

Schmidt, et al., "Stimulation of Soluble Coronary Arterial Guanylate Cyclase by Sin–1," *Eur J. Pharmacol.* 122:75–79 (1986).

Southern, et al., "Inhibition of Insulin Secretion by Interleukin–1β and Tumor Necrosis Factor–α via an L–Arginine–Dependent Nitric Oxide Generating Mechanism," *FEBS Let.,* 276:42–44 (1990).

Stavert, et al., "Nitric Oxide and Nitrogen Dioxide . . . Concentrations for Brief Periods," *Inhal Toxicol,* 2:53–67 (1990).

Stuart–Smith, et al., "Epithelium, Contractile Tone, and Responses to Relaxing Agonists in Canine Bronchi," *J. Appl. Physiol.* 69:678–685 (1990).

Suzuki, et al., "The Relationship Between Tissue Levels of Cyclic GMP and Tracheal Smooth Muscle Relaxation in the Guinea–Pig," *Clin. Pharmacol. Physol.* 13:39–46 (1986).

Swami, et al., "The Pulmonary Physician and Critical Care," *Thorax,* 47:555–562 (1992).

Valliance, et al., "Biology and Clinical Relevance of Nitric Oxide," *Br. Med. J.,* 309:453–457 (1991).

Vlahakes, et al., "The Pathophysiology of Failure in Acute Right Ventricular Hypertension: Hemodynamic and Biochemical Correlations," *Circulation,* 63:87–95 (1981).

Von der Leyen, et al., "In Vivo Gene Transfer to Prevent Neointima Hyperplasia After Vascular Injury: Effect of Overexpression of Constitutive Nitric Oxide Synthase," *FASEB J.* 8, absr. No. 4651 (1994).

Young, et al., "The Body's Vital Poison," *New Scientist,* 137:36–40 (1993).

Zapol, et al., "Pulmonary Circulation During Adult Respiratory Distress Syndrom," *Mercel Dekker,* 241–273 (1985).

Zapol, et al., "Regional Blood Flow During Simulated Diving in the Conscious Weddell Seal," *J. Appl. Physiol.,* 47:968–973 (1979).

Zapol, et al., "Pulmonary Hypertension in Severe Acute Respiratory Failure," *N.E. J. Med.,* 296:476–480 (1977).

PCT Search Report in Application No. PCT/US93/06091, mailed Nov. 15, 1993.

PCT Search Report issued in application PCT/US91/09111, mailed Apr. 15, 1992.

Supplementary European Search Report for corresponding EP application No. 92902708.4, mailed Oct. 19, 1993.

Johnson et al., ("Cardioprotective Effects of Authentic Nitric Oxide in Myocardial Ischemia with Reperfusion," *Critical Care Med.* 19:244–252 (1991).

Ovize et al, "Inhibition of coronary artery thrombosis . . . " J–Cardiovasc.–Pharmacol. 16(4) pp. 641–645. (Abstract), 1990.

Just et al., "Nitric oxide dependence . . . " Z–Kardiol 80 Suppl 5: pp. 29–33 (Abstract), 1991.

Plotkine et al., "Oral administration . . . " Eur.–J–Pharmacol 201(1) pp. 115–116 (Abstract), 1991.

Yao et al., "Endogenous and Exogenous . . . " Circulation, 92(4) pp. 1005–1010. (Abstract), 1995.

TREATMENT OF VASCULAR THROMBOSIS AND RESTENOSIS WITH INHALED NITRIC OXIDE

This is a division of copending application Ser. No. 08/389,304, filed Feb. 16, 1995.

STATEMENT AS TO FEDERALLY SPONSORED RESEARCH

Work on this invention was supported, in part, with funds from the United States government (USPHS grants HL42397 and HL45895). The government therefore has certain rights in the invention.

BACKGROUND OF THE INVENTION

This invention relates to methods of treating, inhibiting or preventing vascular thrombosis and methods of treating, inhibiting or preventing arterial restenosis resulting from excessive intimal hyperplasia.

A thrombosis, i.e, the formation or presence of a blood clot within a blood vessel, may result from physical injury of an arterial wall by a vascular interventional procedure such as percutaneous transluminal coronary angioplasty ("PTCA"; a type of balloon angioplasty) or coronary bypass surgery. Thrombosis may also result from progression of a natural disease, such as atherosclerosis. Various agents, including aspirin, prostaglandin $E_1$, selective thromboxane $A_2$ inhibitors, selective thrombin inhibitors, platelet receptor GPIIb/IIIa blockers, tissue plasminogen activator, streptokinase, heparin and kistrin have been used as antithrombotics. See, e.g., Yasuda et al. (*Circulation* 83:1038 (1991)); and Gold et al., (*Circulation* (Supplement IV) 83:IV26 (1991)). Currently available antiplatelet agents include aspirin, ticlopidin, monoclonal antibodies, nitroglycerin and sodium nitroprusside.

Another unwanted result of arterial injury from vascular interventional procedures is arterial restenosis. For example, PTCA has been used extensively to open occluded arteries in both the coronary and peripheral vascular systems. Although initially successful in over 95 percent of cases, a gradual renarrowing or reocclusion process, known as restenosis, occurs within six months in 30 to 50 percent of the patients.

Vascular interventional procedures tend to damage the vascular wall. Such injury triggers the proliferation of vascular smooth muscle cells, resulting in intimal hyperplasia. This proliferation may be due in part to the effects of platelet-derived growth factors released by platelets which adhere to the site of arterial injury. Excessive intimal hyperplasia leads to restenosis, i.e., a re-narrowing of the arterial lumen. Thus, arterial restenosis can severely limit the long-term effectiveness of vascular interventional procedures.

SUMMARY OF THE INVENTION

It has been discovered that inhaled nitric oxide (NO) gas increases blood vessel patency after lysis of a thrombus at the site of a critical stenosis, without causing any systemic hemodynamic effects. The antithrombotic effects of inhaled NO persist after the cessation of NO inhalation. It has also been discovered that inhaled NO inhibits arterial restenosis resulting from excessive intimal hyperplasia.

Accordingly, in one aspect, the invention features a method for treating, inhibiting or preventing a thrombosis in a mammal, by causing the mammal to inhale a therapeutically effective amount of gaseous NO. The thrombosis may be associated with a disease or injury.

In another aspect, the invention features a method for treating, inhibiting or preventing arterial restenosis in a mammal, by causing the mammal to inhale a therapeutically effective amount of gaseous NO. The arterial restenosis may be associated with a disease or injury.

A second compound which potentiates the beneficial effects of inhaled NO may be administered to a mammal, in conjunction with NO inhalation. One means whereby the second compound could potentiate the beneficial effects of NO inhalation is by prolongation of the effect of inhaled NO in target tissues, or cells that interact with the target tissues, without causing undesirable systemic vasodilation and concomitant decrease in systemic blood pressure. More particularly, prolonging the antithrombotic and/or intimal hyperplasia-inhibiting effect of inhaled NO may be accomplished by administering a phosphodiesterase-inhibiting agent in conjunction with (i.e., before, during or immediately after) NO inhalation. Preferred phosphodiesterase inhibitors are those that selectively inhibit cGMP-specific phosphodiesterases, while minimally affecting the breakdown of adenosine 3',5'-cyclic monophosphate (cAMP) by other phosphodiesterases. A preferred phosphodiesterase inhibitor displaying the aforementioned specificity is Zaprinast™ (M&B 22948; 2-o-propoxyphenyl-8-azapurine-6-one, Rhone-Poulenc Rorer, Dagenham Essex, UK). Other cGMP-specific phosphodiesterase inhibitors are known and may be substituted for Zaprinast™.

Another means whereby the second compound could potentiate the beneficial effects of NO inhalation is by prolongation of the in vivo half-life of NO. That may be accomplished, for example, by administering superoxide dismutase. Superoxide dismutase removes superoxide radicals, which react with NO.

In other preferred embodiments, a second antithrombotic agent which augments the beneficial antithrombotic effects of inhaled NO may be administered to a mammal in conjunction with the inhaled NO. Examples include aspirin, ticlopidine, monoclonal antibodies, nitroglycerin, and sodium nitroprusside.

As used herein, "acute ischemic coronary syndrome" means acute occlusion of a coronary artery, e.g., acute myocardial infarction, unstable angina, crescendo angina, angina pectoris, coronary intermediate syndrome, angina pectoris status post thrombolysis and angina pectoris status post PTCA.

As used herein, "antithrombotic agent" means an agent that inhibits thrombus formation, stimulates thrombolysis, i.e., thrombus dissolution, or both.

As used herein, "intimal (or neointimal) hyperplasia" means proliferation of arterial smooth muscle cells in the intima, in response to arterial endothelial denudation.

As used herein, "revascularization" means reestablishment of blood supply to a part of the mammalian body.

As used herein, "target cells" means non-pulmonary cells that interact directly with NO, following NO inhalation, to mediate a beneficial effect in the inhibition, prevention or treatment of thrombosis or arterial restenosis.

As used herein, a "therapeutically effective concentration of gaseous NO" is a concentration that induces one or more of the following in a given patient: relief of chest pain, relief of shortness of breath, resolution of ischemic electrocardiographic changes, and improved coronary artery blood flow (which may be shown by angiography).

As used herein, a "therapeutically effective" amount of a phosphodiesterase inhibitor is an amount that increases the duration (i.e., half-time) or magnitude of the therapeutic effect of gaseous NO.

As used herein, "thrombosis" means the formation or presence of a blood clot within a blood vessel, which clot may cause infarction or ischemia of tissues supplied by the vessel.

As used herein, "arterial restenosis" means an abnormal narrowing of an arterial lumen as a result of excessive (neo)intimal hyperplasia.

As used herein, "vascular interventional procedure" means any surgical procedure that involves an anatomical disruption or a mechanical disturbance of a blood vessel. A non-exclusive list of vascular interventional procedures includes balloon angioplasty, laser angioplasty, coronary artery surgery, atherectomy and coronary artery stents.

The methods herein disclosed are useful for treating, inhibiting or preventing thrombosis, such as may result from a naturally occurring disease, e.g., athrosclerosis, or from a vascular interventional procedure, e.g., angioplasty or coronary bypass surgery. The methods herein disclosed are also useful for treating, inhibiting or preventing arterial restenosis resulting from excessive intimal hyperplasia. Such arterial restenosis is a frequent complication associated with vascular interventional procedures, such as PTCA or coronary bypass surgery.

According to this invention, NO gas may be administered:

(a) continuously or intermittently;

(b) in the absence of tobacco smoke;

(c) at a concentration between 0.1 and 300 parts per million (ppm), preferably between 1.0 and 200 ppm, and most preferably between 20 and 100 ppm;

(d) as a mixture including NO, oxygen ($O_2$), and nitrogen ($N_2$) or other inert gases, preferably having an $FiO_2$ (i.e., proportion of $O_2$, by volume) of 0.20 to 0.99, the proportion of $O_2$ in air being 0.21, and where the NO gas is mixed with the $O_2$-containing gas shortly before inhalation (e.g., less than 5 minutes before inhalation, and preferably less than one minute before inhalation); and (e) in such a way that the concentration of $NO_2$ is monitored and kept within safe limits (e.g., less than 1 ppm).

An important advantage of this invention is that inhaled NO does not induce systemic vasodilation and concomitant acute systemic hypotension. Systemic vasodilation is an undesirable, potentially dangerous side effect associated with sustained systemic NO release from oral or intravenously administered NO donor compounds which have been used to inhibit thrombosis or excessive intimal hyperplasia.

Other features and advantages of the invention will be apparent from the following description of the preferred embodiments thereof, and from the claims.

DETAILED DESCRIPTION

Thrombosis

Figure 1A:
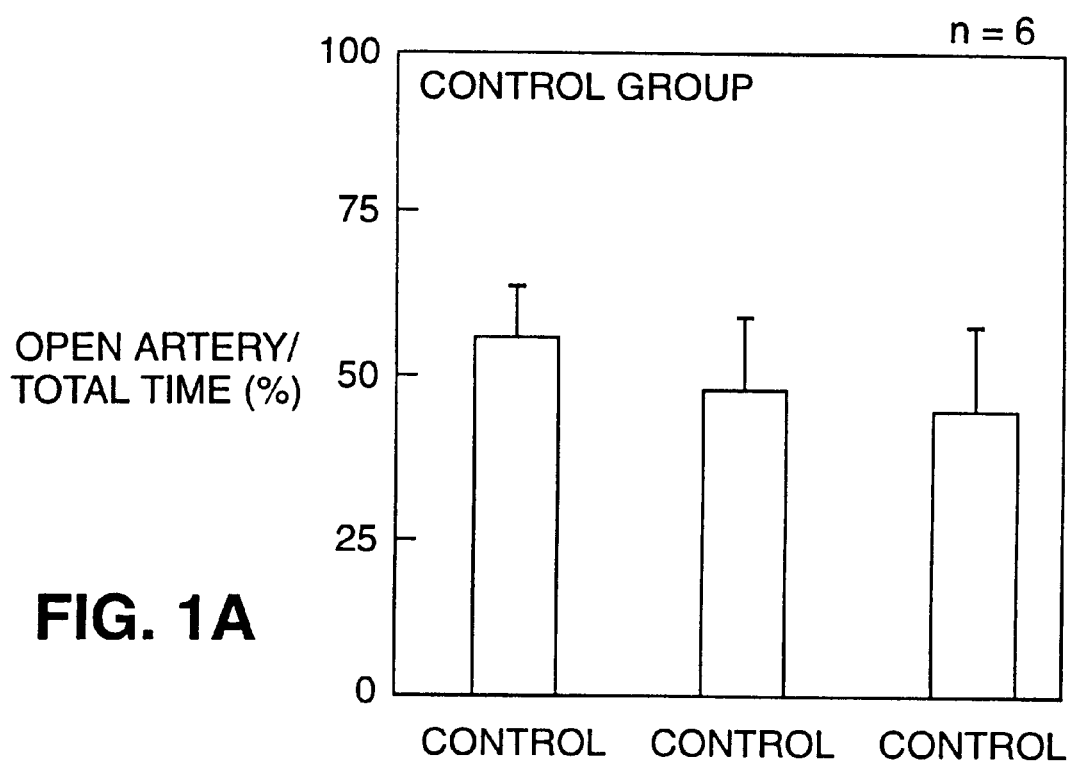
FIG. 1A is a graph comparing open arterial time (as a percentage of total time) for the control group before, during and after zero ppm NO inhalation, in the canine coronary artery thrombosis model.

The invention provides a simple, rapid, selective and efficacious method for treating, inhibiting or preventing a vascular thrombosis in a mammal, such as a human patient. The thrombosis to be treated, inhibited or prevented may result from any of the various causes of thromboses. For example, the type of thrombosis may be a posttraumatic arterial thrombosis. The thrombosis may be at any one of various locations in the mammalian body. For example, the thrombosis location may be arterial, venous, coronary, cerebral, femoral, renal or placental. Preferably, the location of the thrombosis treated, inhibited or prevented is not pulmonary.

Coronary thromboses are often associated with an acute ischemic coronary syndrome. Any thrombosis-related acute ischemic coronary syndrome may be treated, inhibited or prevented by the administration of inhaled NO, according to this invention. The thrombosis-related acute ischemic coronary syndrome may be associated with, e.g., an artery-occluding disease or a vascular interventional procedure. Thrombosis-related acute ischemic coronary syndromes include, but are not limited to, myocardial infarction, unstable angina pectoris, thrombosis after coronary revascularization, and reocclusion after coronary thrombolysis. Coronary revascularization may be accomplished by various known vascular interventional procedures, e.g., PTCA, laser angioplasty, coronary artery bypass grafting, coronary artery atherectomy or coronary artery stents.

Inhaled NO may be used, according to this invention, to treat a mammal that has been identified as having an existing thrombosis. Mammals, and humans in particular, are known to display various signs and symptoms relating to the existence of a thrombosis, and may be identified thereby. The recognition of such signs and symptoms is within the skill of medical practitioners. Signs and symptoms of a thrombosis in a human patient include, but are not limited to, the following: chest pain, shortness of breath, paralysis, limb pain, myocardial infarction, angina pectoris, unstable angina pectoris, crescendo angina pectoris, ischemic congestive heart failure, cardiogenic shock, peripheral vascular disease and ischemic limb. In one embodiment of this invention, the identified mammal is a human who has a thrombosis, and the thrombosis to be treated by NO inhalation is manifested as a myocardial infarction.

Alternatively, inhaled NO also may be used to inhibit or prevent thrombosis development in a mammal that does not have an existing thrombosis but has been identified as being at risk of developing a thrombosis. Certain existing pathological conditions, e.g., atherosclerosis, are known to put an individual at risk of developing a thrombosis. In addition, certain vascular interventional procedures, e.g., balloon angioplasty and coronary artery bypass surgery, are known to put an individual at risk of developing a thrombosis. Accordingly, individuals diagnosed as having pathological conditions with which an increased risk of thrombosis is associated, individuals who have undergone one or more vascular interventional procedures, and individuals for whom one or more vascular interventional procedures are imminent, may be advantageously treated according to this invention.

Similarly, the identified mammal may be a human at risk of developing a thrombosis, where the risk is associated with an artery-occluding disease such as atherosclerosis. Individuals with such pathological conditions may be identified by methods known to medical practitioners trained in the relevant areas of medical practice.

In another embodiment of this invention, the risk is associated with a vascular interventional procedure such as angioplasty. In a particularly preferred embodiment, the identified mammal is a human at risk of developing a thrombosis as a result of a PTCA procedure.

Arterial Restenosis

The invention provides a simple, rapid, selective and efficacious method for treating, inhibiting or preventing arterial restenosis resulting from excessive intimal hyperplasia. Excessive intimal hyperplasia and arterial restenosis frequently occur following vascular interventional procedures such as angioplasty of any vessel (e.g., carotid, femoral, coronary, etc.); or any coronary revascularization procedure, including balloon angioplasty, laser angioplasty, coronary artery bypass grafting, atherectomy or coronary artery stents.

Inhaled NO may be used, according to this invention, to treat a mammal that has been identified as having an existing arterial restenosis. Mammals are known to display various signs and symptoms relating to the existence of an arterial restenosis, and may be identified thereby. The recognition of such signs and symptoms is within the skill of medical practitioners. Signs and symptoms of a arterial restenosis in a mammal include, but are not limited to, the following: chest pain, shortness of breath, electrocardiographic changes and coronary angiographic findings. The objective of treating an existing arterial restenosis with inhaled NO is to reduce the thickness of the intima of a restenosed artery, so as to increase the diameter of the arterial lumen, i.e., reduce the pathological stricture.

Alternatively, inhaled NO may be used, according to this invention, to inhibit or prevent arterial restenosis in a mammal (e.g., a human) that does not have an existing arterial restenosis but has been identified as being at risk of developing an arterial restenosis. Certain vascular interventional procedures, e.g., PTCA and coronary bypass surgery, can cause arterial trauma. Arterial trauma is known to lead to excessive intimal hyperplasia and arterial restenosis. Therefore, those procedures put a patient at risk of developing an arterial restenosis. Accordingly, individuals who have undergone one or more vascular interventional procedures, and individuals for whom one or more vascular interventional procedures are imminent, may be advantageously treated according to this invention.

The inhaled NO is, for example, administered to a human patient who is scheduled to undergo a vascular interventional procedure. Inhaled NO may be administered in advance of a vascular interventional procedure, to minimize the amount of intimal thickening that takes place following the arterial trauma normally associated with vascular interventional procedures. A patient receiving inhaled NO as a preventive measure before a vascular interventional procedure may or may not have an existing arterial restenosis. Alternatively, inhaled NO may be administered to a patient who has already undergone a vascular interventional procedure. In that situation, administration of the inhaled NO preferably will begin within hours of the vascular interventional procedure. Of course, one of skill in the art will recognize that inhaled NO may be administered before, during and after a vascular interventional procedure. Regardless of whether the inhaled NO is administered before, during or after the procedure, or all three, the inhaled NO may be administered continuously or intermittently.

Administration of Inhaled NO

Inhaled NO is preferably administered from a source of stored, compressed NO gas. Compressed NO gas may be obtained from a commercial supplier such as Airco (Murray Hill, N.J.), typically as a mixture of 200–800 ppm NO in pure $N_2$ gas. The source of NO can be 100% NO, or diluted with $N_2$ or any other inert gas (e.g., helium). It is vital that the NO be obtained and stored as a mixture free of any contaminating $O_2$ or higher oxides of nitrogen, because such higher oxides of nitrogen (which can form by reation of $O_2$ with NO) are potentially harmful to lung tissues. If desired, purity of the NO may be demonstrated with chemiluminescence analysis, using known methods, prior to administration to the patient. Chemiluminescence NO–$NO_x$ analyzers are commercially available (e.g., Model 14A, Thermo Environmental Instruments, Franklin, MA). The NO–$N_2$ mixture may be blended with air or $O_2$ through, for example, calibrated rotameters which have been validated previously with a spirometer. The final concentration of NO in the breathing mixture may be verified with a chemical or chemiluminescence technique well known to those in the field (e.g., Fontijin et al., *Anal. Chem.* 42:575 (1970)). Alternatively, NO and $NO_2$ concentrations may be monitored by means of an electrochemical analyzer. Any impurities such as $NO_2$ can be scrubbed by exposure to NaOH solutions, baralyme, or sodalime. As an additional control, the $FiO_2$ of the final gas mixture may also be assessed. If desired, the ventilator may have a gas scavenger added to the expiratory outlet to ensure that significant amounts of NO will not escape into the adjacent environment.

In a hospital or emergency field situation, administration of NO gas could be accomplished, for example, by attaching a tank of compressed NO gas in $N_2$, and a second tank of oxygen or an oxygen/$N_2$ mixture, to an inhaler designed to mix gas from two sources; by controlling the flow of gas from each source, the concentration of NO inhaled by the patient can be maintained at an optimal level. NO gas may also be mixed with room air, using a standard low-flow blender (e.g., Bird Blender, Palm Springs, Calif.). NO may be generated from $N_2$ and $O_2$ (i.e., air) by using an electric NO generator. Such a generator is described in Zapol U.S. patent application 07/850,383 (notice of allowance issued), which is hereby incorporated by reference. In addition, NO may be provided intermittently from an inhaler. The use of an inhaler may be particularly advantageous if a phosphodiesterase inhibitor is administered, orally or by inhalation, in conjunction with the NO.

NO may be administered to a mammal identified as having a thrombosis or arterial restenosis, or a mammal identified as being at risk for developing a thrombosis or arterial restenosis, at a concentration of from 0.1 ppm to 300 ppm in air, pure oxygen, or another suitable gas or gas mixture, for as long as needed. Preferably, the concentration will be between 1.0 and 200 ppm; and most preferably between 20 and 100 ppm (e.g., 30 ppm, 40 ppm, 50 ppm, 60 ppm or 80 ppm). The concentration may temporarily increased for short periods of time: e.g., 5 min at 300 ppm NO, when an immediate dramatic effect is desired. For the reasons explained below, concomitant treatment with a phosphodiesterase inhibitor may decrease the total dosage of NO required (or allow intermittent dosage) to produce a satisfactory anti-thrombotic or anti-restenosis effect.

For treatment, inhibition or prevention of arterial restenosis, it may be necessary to administer inhaled NO by nasal prongs, mask, tent, intra-tracheal catheter or endotracheal tube, for an extended period, i.e., days or weeks. The administration may be continuous, during the extended period. Alternatively, administration could be intermittent during the extended period. The administration of gaseous NO may be via spontaneous or mechanical ventilation.

Assessment of Effects of Inhaled NO

When inhaled NO is administered to treat, inhibit or prevent thrombosis or arterial restenosis, it is desirable to monitor the effects of the NO inhalation. Such monitoring can be used, in a particular individual, to verify desirable effects and to identify undesirable side effects that might occur. Such monitoring is also useful in adjusting dose level, duration and frequency of administration of inhaled NO in a given individual.

Preferably, the effects of inhaled NO on a patient would be assessed by one or more of the following: clinical manifestations such as chest pain; electrocardiography; serial analyses of vascular patency by ultrasound, coronary angiography or other means; and increases in levels of cGMP in plasma or platelets.

Phosihodiesterase Inhibitors

NO decomposes rapidly by reacting with molecular oxygen to produce nitrite and nitrate. In addition, NO entering the blood is rapidly inactivated by tight binding to hemoglobin. For these reasons, NO has only a short half-life in arterial blood. This means that inhaled NO advantageously avoids systemic vasodilation, an undesirable, potentially dangerous side effect associated with sustained systemic NO release from NO donor compounds.

It may be desirable to prolong the beneficial effects of inhaled NO within the target cells or within cells interacting with the target cells in the lung. In the context of thrombosis inhibition, prevention and treatment, circulating platelets are the target cells. In the context of arterial restenosis inhibition, prevention and treatment, circulating platelets (and possibly white cells) are the cells which interact with the target cells in the vasculature.

In determining how to prolong the beneficial effects of inhaled NO, it is useful to consider that one of NO's in vivo effects is activation of soluble guanylate cyclase, which stimulates production of guanosine-3',5'-cyclic monophosphate (cGMP). At least some of the beneficial effects of NO appear to result from NO's stimulation of cGMP biosynthesis. Accordingly, in a preferred embodiment of the invention, a phosphodiesterase inhibitor is administered in conjunction with NO inhalation, to inhibit the breakdown of cGMP by endogenous phosphodiesterases.

The phosphodiesterase inhibitor may be introduced into the mammal by any suitable method, including via an oral, transmucosal, intravenous, intramuscular, subcutaneous or intraperitoneal route. Alternatively, the inhibitor may be inhaled by the mammal. For inhalation, the phosphodiesterase inhibitor is advantageously formulated as a dry powder or an aerosolized solution having a particle or droplet size of less than 10 $\mu$m for optimal deposition in the alveoli, and may optionally be inhaled in a gas containing NO.

A preferred phosphodiesterase inhibitor is Zaprinast™ (M&B 22948; 2-o-propoxyphenyl-8-azapurine-6-one; Rhone-Poulenc Rorer, Dagenham Essex, UK). Zaprinast™ selectively inhibits the hydrolysis of cGMP with minimal effects on the breakdown of cAMP in vascular smooth muscle cells (Trapani et al., J. Pharmacol. Exp. Ther. 258:269 (1991); Harris et al., J. Pharmacol. Exp. Ther. 249:394 (1989); Lugnier et al., Biochem. Pharmacol. 35:1743 (1986); Souness et al., Br. J. Pharmacol. 98:725 (1989)). When using Zaprinast™ according to this invention, the preferred routes of administration are intravenous or oral. The suitable dose range may be determined by one of ordinary skill in the art. A stock solution of Zaprinast™ may be prepared in 0.05N NaOH. The stock can then be diluted with Ringer's lactate solution to the desired final Zaprinast™ concentration, immediately before use.

This invention may be practiced with other phosphodiesterase inhibitors. Various phosphodiesterase inhibitors are known in the art, including dipyridamole and theophyline. As with Zaprinast™, the route of administration and suitable dose range may be determined by one of ordinary skill in the art.

Other Antithrombotic Agents in Conlunction with Inhaled NO

Thrombosis may be treated by agents that inhibit thrombus formation, agents that stimulate thrombolysis, i.e., thrombus dissolution, or both. Examples of antithrombotic agents are aspirin, streptokinase, urokinase, tissue plasminogen activator ("t-PA"), met-t-PA (i.e., t-PA with an N-terminal methionine residue), FE1X (a t-PA analog) heparin, hirudin and Hirulog™ (a hirudin analog). Other antithrombotic agents could also be used in the practice of this invention. One or more such antithrombotic agents may be administered to a mammal before, during or after treatment with inhaled NO, so that their separate antithrombotic activity is advantageously used to augment the antithrombotic effect(s) of inhaled NO.

For example, in one embodiment of this invention, an appropriate dose of t-PA is administered before, during or immediately after NO inhalation, to treat thrombosis. While the inhaled NO is inhibiting or preventing the formation of new thrombi, the t-PA will stimulate the dissolution of: (1) thrombi already present at the time inhaled NO was administered, or (2) thrombi formed (albeit at a reduced rate) during or immediately after the NO inhalation. The selection of appropriate antithrombotic agents to be administered in conjunction with inhaled NO, and the selection of the appropriate dosage and route of administration of those antithrombotic agents is within ordinary skill in the art.

In a preferred embodiment of this invention, aspirin is administered before, during or immediately after NO inhalation, to treat thrombosis. The preferred aspirin dose range is 81 to 325 mg (orally) per day.

While the two aspects of this invention (i.e., thrombosis and arterial restenosis) have been described separately, it should be appreciated that an individual may already have, or be at risk of developing, both a thrombosis and arterial restenosis. Under such circumstances, both aspects of the invention could be practiced at the same time, in the same individual, with a single administration of inhaled NO.

EXPERIMENTAL INFORMATION

Thrombosis Experiments

The antiplatelet effects of NO have been assessed in a recognized canine model of acute coronary thrombolysis after thrombus formation. The canine model used was essentially as described by Yasuda et al. (*J. Am. Coll. Cardiol.* 13:1409 (1989)) and Gold et al. (*Circulation* (suppl. IV) 83:IV26 (1991)).

Twenty-five adult mongrel dogs (20–25 kg) of either sex were anesthetized with pentobarbital (30 mg/kg body weight). Supplemental pentobarbital was administered as required to maintain general anesthesia. The dogs' tracheas were intubated and their lungs were mechanically ventilated at 15 breath/min and 10–15 ml/kg with a ventilator at $FiO_2$ within 21–35% (Hudson Ventronics, Tenecula, Calif.) and adjusted to maintain the arterial blood $O_2$ between 80 and 100 torr. The oxygen saturation was continuously monitored during the experiment, using a pulse oximeter (Nellcor, Inc., Haywood, Calif.).

The femoral artery and vein were cannulated with a polyvinyl chloride catheter for continuous arterial pressure, blood sampling and infusion. Lidocaine 0.1 mg/kg/min i.v., was given when arrhythmias occurred. Thoracotomy was performed through the left fifth intercostal space. The pericardium was opened and suspended to create a pericardial cradle. The left anterior descending artery was dissected out free, and a 2.5 cm segment was isolated distal to the first diagonal branch. One milliliter of blood was withdrawn for thrombus formation. A 0.7 mm i.d. catheter was inserted into a side branch of the isolated left anterior descending coronary artery segment, and an ultrasonic flow probe (T101 Transonic System, Inc., Ithaca, N.Y.) was placed on the proximal portion of the artery for continuous blood flow monitoring. A 2 mm wide plastic wire (Mass Gas and Electric Supply, Watertown, Mass.) was progressively constricted around the left anterior descending artery, just distal to the proposed site of thrombus formation, to limit blood flow to 50±10% of baseline. Previous angiographic study has shown this to decrease the luminal diameter by more than 90%.

The isolated left anterior descending coronary artery was traumatized by four consecutive external compressions with blunted forceps during 3–5 seconds, to damage the endothelium and promote thrombus adherence. Snare occlusions were made distal to the probe and proximal to the constriction site. Thrombin (0.1 ml of 100 units/ml; Thrombinar, Armour Pharmaceutical, Kankakee, Ill.) mixed with 0.3 ml of blood was injected through the side branch catheter into the emptied coronary artery segment to induce thrombus formation. After 10 minutes, the proximal snare was released. Two minutes later, the distal snare was released. Ten minutes after thrombus formation, a heparin bolus (75 UI/kg) was administered intravenously and followed by a continuous heparin infusion (50 UI/kg/h). After a 30-minute period of stable occlusion, recombinant t-PA boluses (0.45 mg/kg; Activase™, Genentech Inc., South San Francisco, Calif.) were administered at 15-minute intervals, until recanalization of the thrombosed coronary artery was achieved or a maximum of four boluses had been administered.

This procedure induced alternating periods of recanalization and reocclusion (defined as less than 25% of poststenotic flow) after initial reflow of the left descending coronary artery. The ratio opening time/total time was recorded as the primary outcome variable. ECG, systemic arterial pressure, left atrial pressure and coronary blood flow were continuously recorded. Animals with: (1) no reperfusion, (2) reperfusion without occlusion, (3) fewer than 3 cycles during the first 45-minute observation period, or (4) death before the end of the first observation period, were excluded from further study.

NO gas (800 ppm NO in nitrogen, Airco, Murray Hill, N.J.) was mixed with room air using a standard low-flow blender (Bird Blender, Palm Springs, Calif.) and then titrated with varying quantities of NO, to maintain a constant $FiO_2$ just prior to delivery to the ventilator. Inspired NO level was continuously monitored by a chemiluminescence $NO-NO_x$ analyzer (Model 14A, Thermo Environmental Instruments, Franklin, Mass.; Fontijin et al., supra). The $FiO_2$ was measured (oxygen meter No. 5590, Hudson, Temecula, Calif.) distal to the reservoir bag after the NO-containing gases were mixed. The exhaled gases, as well as those discharged from the chemiluminescence analyzer, were scavenged by use of a venturi exhalation trap maintained at negative atmospheric pressured by the laboratory's central vacuum system. The ambient $NO/NO_2$ levels, as measured intermittently by chemiluminescence, did not increase during the experiments. At each time samples were taken and methemoglobin levels were measured. Heart rate, blood pressure and coronary flow were monitored and recorded continuously.

After a 45 minute baseline study period (pretreatment period) the animals were divided into four groups: Group A (n=6) was given 0 ppm inhaled NO (i.e., air) for 45 minutes; Group B (n=6) was given 20 ppm inhaled NO for 45 minutes; Group C (n=6) was given 80 ppm inhaled NO for 45 minutes and Group D (n=6) was given 200 ppm for 45 minutes. All groups of animals were then observed for a third study period beginning with the cessation of NO administration and lasting 45 minutes (posttreatment period).

In vitro Measurement of Platelet Aarrecation

Blood from 8 dogs was collected in 0.01M citrate and centrifuged at room temperature at 370×g for 5 minutes, for the preparation of platelet-rich plasma (PRP), and at 1200×g for 10 minutes, for the preparation of plateletpoor plasma (PPP). PRP was exposed only to plastic containers or, during testing, siliconized glassware. The platelet count (Thrombocounter C™ platelet counter, Coulter Electronics, Inc., Hialeah, Fla. of PRP was adjusted by dilution with PPP to obtain $300,000/mm^3 \pm 10\%$. PRP was then aliquoted into cuvettes incubated at 37° C. with magnetic stirring (1000 rpm) in a dual channel aggregometer (Model 440, Chrono-Log Corp., Havertown, Pa.). Light transmission was continuously recorded on a recorder (Model 707, Chrono-Log Corp., Havertown, Pa.). The aggregation sample tube was obstructed with a rubber cap and two 19 gauge needles (Sherwood Medical, St. Louis, Mo.) were placed through this cap, allowing the delivery of a mixture of NO gas and oxygen above the PRP. The inlet needle was connected via a flowmeter to a gas reservoir into which a mixture of NO gas, air and oxygen titrated as described above was delivered. The NO concentration was continuously monitored by the chemiluminescence $NO-NO_x$ analyzer. A needle valve allowed regulation of the flow through the sample to approximately 40 ml/min. Positive pressure was maintained in the system by having the outlet needle connected to a recipient flask filled with 5 cm of water in which constant bubbling was maintained.

ADP-induced platelet aggregometry studies were performed after the exposure of the test cuvette containing 450 $\mu$l of adjusted PRP to the NO gas mixture for 10 minutes. Gas administration was continued during the measurement of ADP-induced aggregation. Platelet aggregation was studied using different aliquots of PRP treated with 20, 80, 200 and 400 ppm of NO, in random order. Control ADP-induced platelet aggregation studies without NO were performed before and after the administration of NO to assess the stability of the PRP preparation. All experiments were completed within 4 hours of blood collection.

Data Analysis

Artery patency was defined as the fraction of the total observation period during which flow was greater than 25% of the basic flow after the initial stenosis was created. Except as noted, results are expressed as mean±SEM. The significance of differences between groups was determined with Student's t-test for paired or unpaired values as appropriate. The significance of the dose response of the effect of NO on ADP-induced platelet aggregation was assessed with two-way analysis of variance. A p value <0.05 was considered significant.

Canine Thrombolysis and Reperfusion Model Results

In each experimental group, the external constrictor reduced left anterior descending artery blood flow by 54±2% of baseline, from 22±2 to 10±1 ml/min. The median number of tPA boluses required to obtain reperfusion was two, with a range of 1 to 4 (Table 1). Cyclic reflow and reocclusion accompanied by electrocardiographic evidence of myocardial injury occurred in all animals except one in which reocclusion did not occur; this animal was excluded from further study.

TABLE 1

Baseline Values of Physiological Parameters

| Parameter Measured | Group A 0 ppm NO (n = 6) | Group B 20 ppm NO (n = 6) | Group C 80 ppm NO (n = 6) | Group D 200 ppm NO (n = 6) |
|---|---|---|---|---|
| Post-stenotic flow (% before stenosis) | 51.7 ± 3.5 | 55.2 ± 3.7 | 51.6 ± 4.7 | 54.6 ± 1.9 |
| Number of tPA boluses | 2.0 ± 0.4 | 1.7 ± 0.2 | 1.8 ± 0.3 | 2.0 ± 0.4 |
| ACT (sec) | 219 ± 16 | 219 ± 14 | 236 ± 5.3 | 196 ± 12.8 |
| $FIO_2$ (%) | 29.0 ± 1.1 | 27.5 ± 1.0 | 32.2 ± 1.5 | 31.6 ± 3.0 |
| Ratio (r) | 55.7 ± 8.5 | 50.6 ± 6.9 | 48.8 ± 2.9 | 45.2 ± 5.6 |
| Hb (mg/dl) | 13.26 ± 1.35 | 14.28 ± 0.85 | 14.08 ± 0.85 | 12.95 ± 0.64 |
| Platelet Ct (× $10^3/mm^3$) | 301 ± 55 | 292 ± 25 | 277 ± 35 | 237 ± 35 |
| MetHb (%) | 0.25 ± 0.17 | 0.10 ± 0.06 | 0.18 ± 0.09 | 0.26 ± 0.09 |

Table 1: "Number of tPA boluses" refers to number of boluses injected; "ACT" refers to activated clotting time; "$FIO_2$" refers to inspired $O_2$ fraction; "Ratio" refers to unoccluded/occluded coronary artery at baseline; "Platelet Ct" refers to platelet count; and "MetHb" refers to methemoglobin (percentage of total hemoglobin). There is no significant difference between the baseline flow rate ratios at 0 ppm (control), 20 ppm, 80 ppm and 200 ppm of inhaled NO (n=6 for each group).

Effects of Inhaled NO on Artery Patency

Figure 1B:
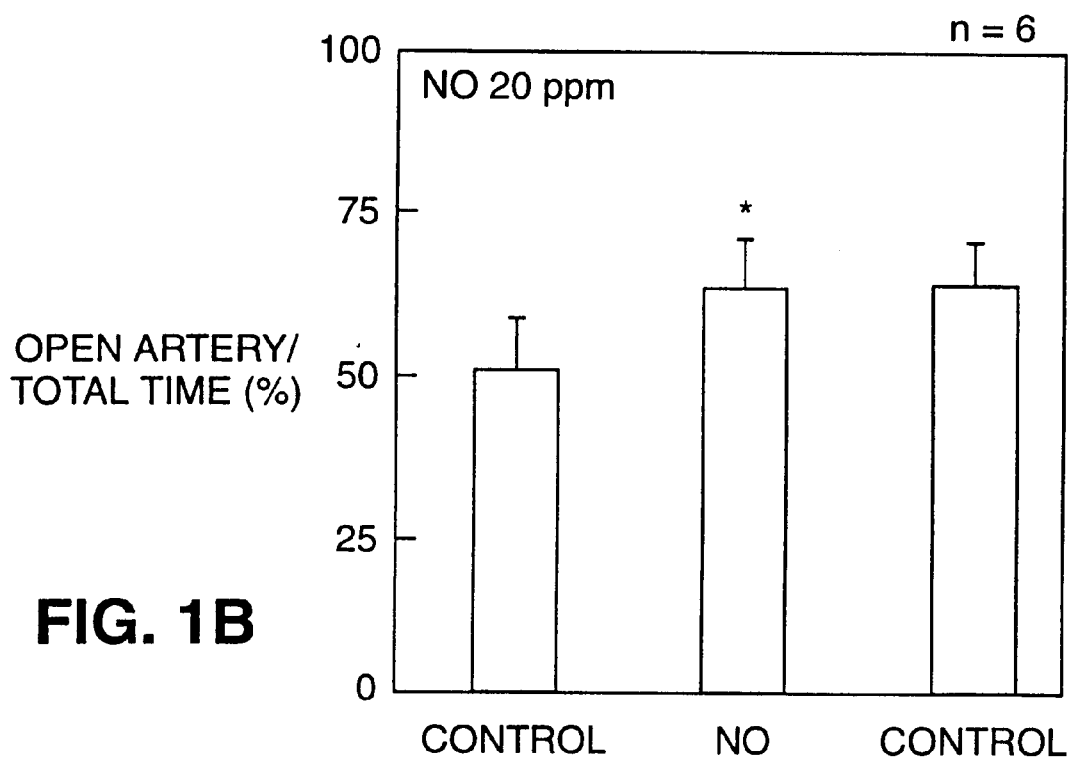
FIG. 1B is a graph comparing open arterial time (as a percentage of total time) for the 20 ppm inhaled NO group before, during and after NO inhalation, in the canine coronary artery thrombosis model. The asterisk indicates value significantly differs from baseline ($p<0.05$).
Figure 1C:
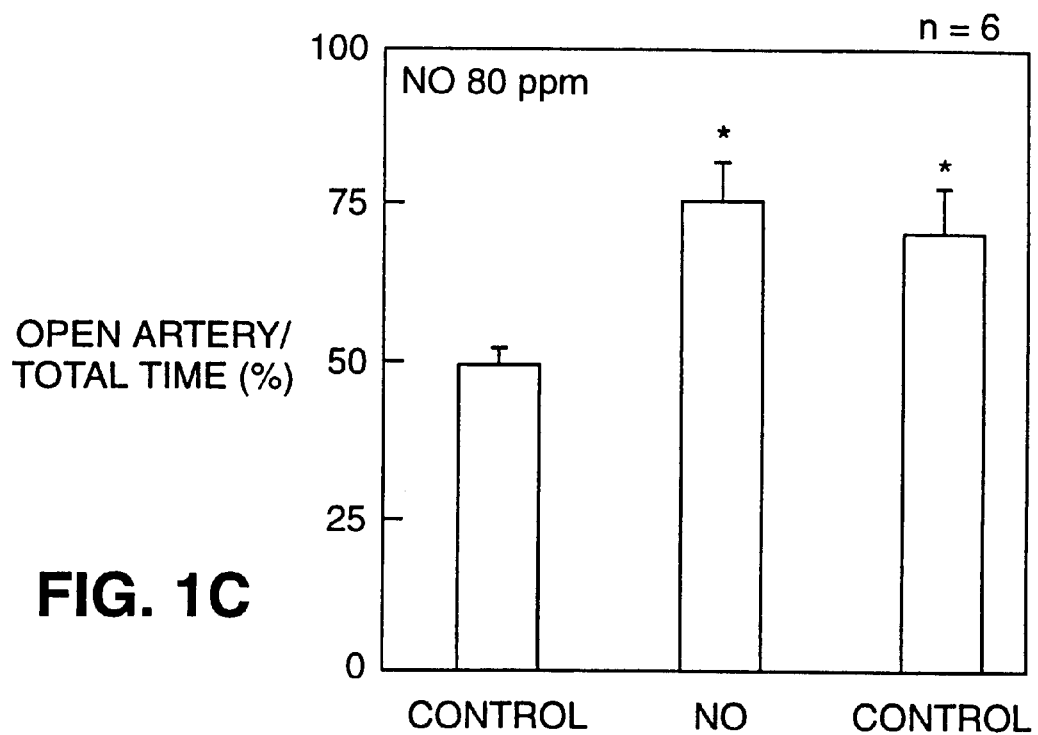
FIG. 1C is a graph comparing open arterial time (as a percentage of total time) for the 80 ppm inhaled NO group before, during and after NO inhalation, in the canine coronary artery thrombosis model. The asterisk indicates value significantly differs from baseline ($p<0.05$).
Figure 1D:
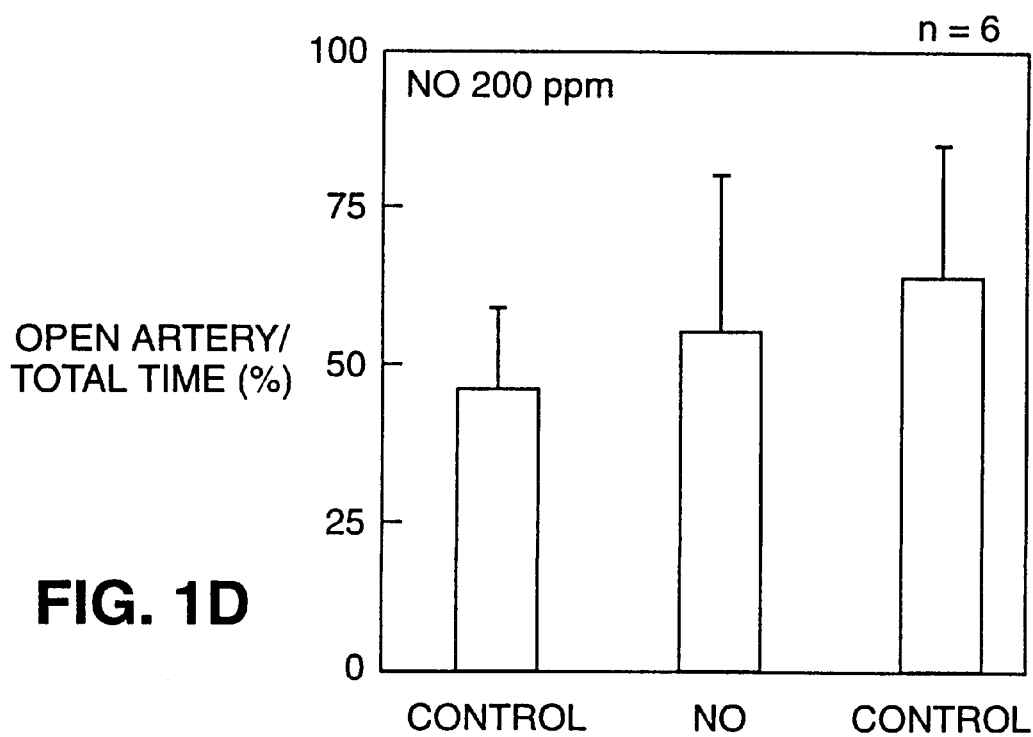
FIG. 1D is a graph comparing open arterial time (as a percentage of total time) for the 200 ppm inhaled NO group before, during and after NO inhalation, in the canine coronary artery thrombosis model.
Figure 2:
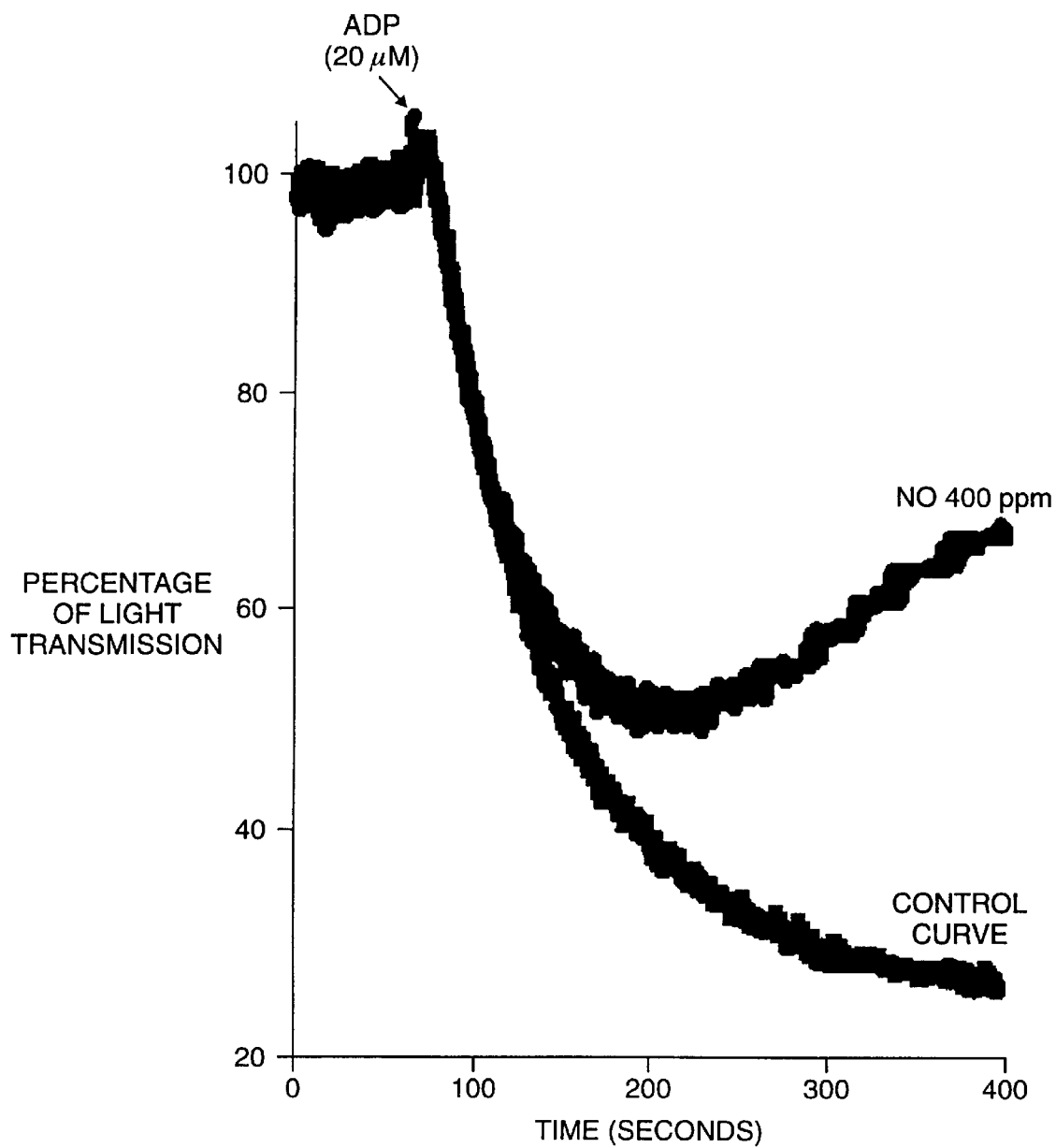
FIG. 2 is a graph showing ADP-induced canine platelet aggregation curves for samples exposed to 0 ppm NO or 400 ppm NO.

In animals receiving 0 ppm inhaled NO (Group A), arterial patency did not change during the three treatment periods (FIG. 1A). In animals receiving 20 ppm inhaled NO (Group B), arterial patency increased from 50.6±6.9% during the pre-inhalation baseline period, to 63.8±7.90 during the inhalation period (p<0.01) (FIG. 1B). In animals receiving 80 ppm inhaled NO (Group C), arterial patency increased from 48.8±2.9% during the pre-inhalation baseline period, to 75.1±6.7% during the inhalation period (p<0.01) (FIG. 1C). In animals receiving 200 ppm inhaled NO (Group D), arterial patency increased from 45.27±5.6% during the pre-inhalation baseline period to 54.8±10.4% during the inhalation period (p=NS) (FIG. 1D). In group C the increased arterial patency observed during the NO inhalation period persisted during the 45-minute postinhalation period (70.1±7.1% vs. baseline, p<0.05).

When the inhalation period arterial patency results from groups B, C, and D were pooled, there was a statistically significant difference between the pooled treatment groups and the control group (p<0.005). When the 45-minute post-inhalation period artery patency results from groups B, C, and D were pooled, there was also a statistically significant difference between the pooled treatment groups and the control group (p<0.005).

Neither platelet count nor blood hemoglobin changed during or after NO administration in any of the groups of animals (Table 3). Methemoglobin levels increased from 0.2±0.1% to 1.1±0.4% in the dogs breathing 200 ppm inhaled NO (Table 3). This increase persisted after the NO administration was stopped and was not seen in dogs receiving lower doses of NO.

Systemic arterial pressure decreased in all groups of dogs during this study, and did not differ between the dogs receiving NO and those who did not (Table 2A). Left atrial pressure was unchanged in all groups of animals throughout the duration of the study (Table 2B).

TABLE 2A

Mean Systemic Arterial Pressure (SAP) (mmHG) Before, During and After NO Inhalation

| NO Treatment | Before | During | After |
|---|---|---|---|
| 0 ppm NO (N = 6) Group A | 89 ± 8 | 82 ± 6 | 80 ± 7 |
| 20 ppm NO (n = 6) Group B | 105 ± 6 | 96 ± 6 | 82 ± 6 |
| 80 ppm NO (n = 6) Group C | 91 ± 5 | 81 ± 9 | 78 ± 7 |
| 200 ppm NO (n = 6) Group D | 94 ± 3 | 95 ± 4 | 93 ± 4 |

Values are expressed as mean ± SEM.

TABLE 2B

Mean Left Atrium Pressure (LAP) (mmHG) Before, During and After NO Inhalation

| NO Treatment | Before | During | After |
|---|---|---|---|
| 0 ppm NO (N = 6) Group A | 5.5 ± 0.6 | 5.4 ± 0.7 | 5.4 ± 0.7 |
| 20 ppm NO (n = 6) Group B | 5.2 ± 1.6 | 4.7 ± 1.4 | 4.6 ± 1.1 |
| 80 ppm NO (n = 6) Group C | 5.3 ± 0.6 | 5.2 ± 0.6 | 4.9 ± 0.6 |

TABLE 2B-continued

Mean Left Atrium Pressure (LAP) (mmHG)
Before, During and After NO Inhalation

| NO Treatment | Before | During | After |
| --- | --- | --- | --- |
| 200 ppm NO (n = 6) Group D | 4.6 ± 1.1 | 4.2 ± 0.9 | 3.7 ± 0.8 |

Values are expressed as mean ± SEM.

Effects of NO on ADP-Induced In Vitro Platelet Aacrecation

Figure 3:
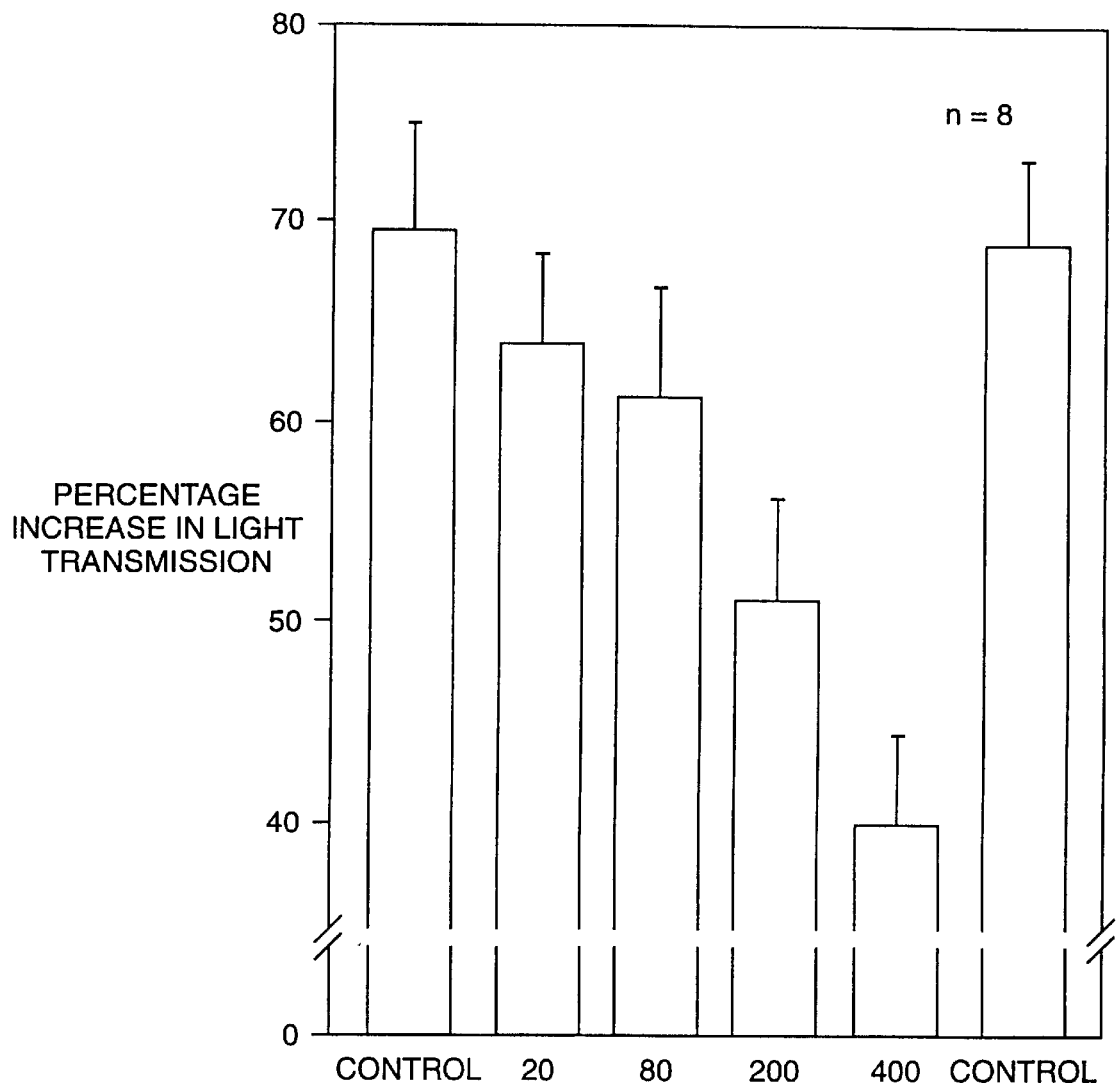
FIG. 3 is a graph summarizing dose response data on the effect of inhaled NO on canine platelet aggregation.

Addition of 20, 80, 200 and 400 ppm NO to the gas mixture above the PRP led to a dose-related decrease in the maximal change in light transmission caused by ADP (FIG. 3). There was no change in the ADP-induced decrease in light transmission in the two control aggregation curves performed at the beginning and end of each study (30.57±5.57% vs. 31.1±4.31%).

TABLE 3

Hematologic Values Before, During and After NO Inhalation

| NO Treatment | Measurement | Before | During | After |
| --- | --- | --- | --- | --- |
| 0 ppm NO Group A (n = 6) | Hb (mg/dl) | 13.2 ± 1.3 | 13.7 ± 0.8 | 12.2 ± 0.7 |
| | Platelet Count (× $10^3$/mm$^3$) | 301 ± 55 | 284 ± 53 | 276 ± 35 |
| | MetHb (%) | 0.22 ± 0.2 | 0.2 ± 0.1 | 0.2 ± 0.2 |
| 20 ppm NO Group B (n = 6) | Hb (mg/dl) | 14.3 ± 0.85 | 12.7 ± 0.7 | 2 ± 1 |
| | Platelet Count (× $10^3$/mm$^3$) | 292 ± 25 | 269 ± 22 | 253 ± 16 |
| | MetHb (%) | 0.1 ± 0.1 | 0.4 ± 0.2 | 0.1 ± 0.02 |
| 80 ppm NO Group C (n = 6) | Hb (mg/dl) | 14.0 ± 0.8 | 11.9 ± 0.3 | 11.1 ± 0.6 |
| | Platelet Count (× $10^3$/mm$^3$) | 277 ± 35 | 238 ± 32 | 209 ± 37 |
| | MetHb (%) | 0.2 ± 0.1 | 0.4 ± 0.1 | 0.3 ± 0.1 |
| 200 ppm NO Group D (n = 6) | Hb (mg/dl) | 12.9 ± 0.6 | 12.2 ± 1.0 | 12.9 ± 0.9 |
| | Platelet Count (× $10^3$/mm$^3$) | 237 ± 35 | 232 ± 44 | 244 ± 40 |
| | MetHb (%) | 0.2 ± 0.1 | 1.1 ± 0.4* | 0.9 ± 0.3 |

Values are expressed as mean ± SEM.
* < 0.05 vs control value.

The above results demonstrate that inhaled NO increases coronary artery patency after lysis of a thrombus at the site of a critical stenosis without producing any systemic hemodynamic effects. They also show that the antithrombotic effects of inhaled NO persist for at least 45 minutes after cessation of NO inhalation. At NO concentrations similar to those obtained in vivo, gaseous NO markedly inhibited ADP-induced platelet aggregation in vitro.

Intimal Hyperplasia Experiments

Neointimal smooth muscle cell hyperplasia is the main pathologic process in human arterial restenosis. Therefore, to elucidate the effect of inhaled NO on the process of restenosis after a vascular interventional procedure such as PTCA, the effect of inhaled NO on intimal hyperplasia was studied, using a rat carotid artery model of arterial injury (Clowes et al., *Laboratory Invest.* 49:327 (1983)), a standard animal model for human neointimal smooth muscle cell hyperplasia.

Arterial Injury

Adult male Sprague-Dawley rats (Charles River Laboratories, Wilmington, Mass.) underwent balloon injury of the common carotid artery in a manner previously shown to bring about neointimal hyperplasia (Clowes et al., supra). Rats weighing 300 to 350 g were anesthetized by intraperitoneal injection of ketamine (60–80 mg/kg) and acepromazine (0.1 mg/kg). Once satisfactory anesthesia had been achieved, a longitudinal midline incision was made and the left carotid artery was isolated via blunt dissection. After further careful dissection of the internal and external carotid bifurcation, the distal external carotid segment was ligated with a 4–0 silk suture. A small arteriotomy was made in the external carotid using microdissecting scissors and a 2 French Fogarty balloon catheter (Baxter Edwards LIS) was inserted through the arteriotomy and advanced approximately two centimeters below the carotid bifurcation. The balloon was filled with enough saline to cause visible distention of the common carotid artery and gently withdrawn to the level of the bifurcation. The balloon catheter was then withdrawn and after allowing back bleeding through the arteriotomy site to eliminate potential thrombus and air bubbles, the external carotid was ligated proximal to the arteriotomy site using 4–0 silk sutures. After visual inspection to insure adequate pulsation of the common carotid artery, the surgical lesion was closed and the animals were allowed to recover from anesthesia.

Chronic NO Inhalation

Chronic NO inhalation was carried out in specially prepared 40 liter acrylic inhalation chambers. The gas mixtures were blended using separately regulated and calibrated flow meters for oxygen, pressurized air and NO stock gases (800 ppm and 10,000 ppm NO in $N_2$, Airco, Murray Hill, N.J.). The effluent gas from the chamber was analyzed periodically throughout the experimental period, to ensure stable $FIO_2$ and NO levels. The $FIO_2$ was measured using a polarographic electrode (Hudson Oxygen Meter 5590, Temecula, Calif.), NO concentration was measured by chemiluminescence (Model 14A, Thermo Environmental Instruments, Inc., Franklin, Mass.); and nitrogen dioxide and nitrogen with higher oxidation states ($NO_x$) were measured by chemiluminescence following conversion of the $NO_x$ to NO by a heated stainless steel oven (850° C.) with 98% efficiency (Model 100B $NO_x$ generator, Thermo Environmental Instruments, Inc., Franklin, Mass.). Fresh soda lime was maintained in the chambers to reduce $NO_x$. NO concentration was maintained at 20 to 80 ppm, depending upon the experiment. Serial measurements revealed $FIO_2$ to be 21% and $NO_x$ to be 3–4 ppm. The gases exiting the exposure chambers, as well as those discharging from the chemiluminescence instrument, were scavenged using a venturi trap maintained at negative atmospheric pressure with reference to the laboratory's central vacuum system.

Control animals were maintained in filtered cages in the same room as the NO-treated animals. The NO exposure was begun 30 to 120 minutes prior to the surgical procedure. During the surgical procedure, the NO-treated group was taken out of the chamber and exposed to NO by a modified face mask fed from the inflow gas tubing of the chambers. Inhaled gas analysis revealed NO levels of 50–80 ppm during the 80 ppm experiments and 10–20 ppm during the 20 ppm surgical experiments. The total time each animal was out of the chamber and under the face mask ranged from 20 to 40 minutes.

Morphometric Analysis

At 1, 3 and 14 days after balloon injury, the rats were euthanized by lethal intraperitoneal injection of sodium pentobarbital or ketamine. A 16 gauge catheter was introduced into the ascending aorta via the left ventricular apex. The descending thoracic aorta was ligated. The animal was then perfused at a pressure of 100 mm Hg with 100 ml of normal saline followed by 50 ml of 2% paraformaldehyde in phosphate buffered saline (PBS). After in vivo fixation for 15 to 30 minutes, both common carotid arteries were isolated and underwent further overnight fixation by immersion in 1% paraformaldehyde in PBS. The tissue was dehydrated using sequentially increasing concentrations of ethanol followed by xylene, and then embedded in paraffin. Cross sections (6 μm) were cut and stained with hematoxylin and eosin and/or elastin for analysis. A single section 7 to 8 mm proximal to the carotid bifurcation was used for analysis in each animal. The section being analyzed was photographed at 100×. The image was digitized using a Kodak 2135™ scanner. The intimal and medial area analyses were performed on a Power Macintosh 8100/80™ computer using the public domain NIH Image program (written by Wayne Rasband at the U.S. National Institutes Of Health and available from the Internet by anonymous ftp from zippy.nimh.nih.gov or on floppy disk from NTIS, 5285 Port Royal Rd., Springfield, Va. 22161; part number PB93-504868). The morphometric analysis was performed with the investigator blinded as to the experimental group.

Statistical Analysis

Statistical analysis was carried out utilizing commercially available Statviewr™ (Abacus Concepts) software for Macintosh™ computers. The experimental group was compared with the control group using an unpaired two tailed t-test. A value of $P<0.05$ was considered statistically significant. All data are represented as mean+/−SEM. The n value refers to the number of animals per group.

Results from Rodent Model of Restenosis

A total of 62 rats underwent the carotid injury procedure. Five of the rats died due to vascular complications during the arteriotomy or the balloon injury, giving a procedure mortality rate of 8%. There was no statistically significant maldistribution of the deaths among the different experimental groups. There were no post-procedure deaths among the 57 rats who survived the initial procedure. All rats, regardless of their experimental group, exhibited normal grooming behavior and activity levels throughout the study. Other than occasional ptosis on the side of the carotid injury, no rats exhibited a gross neurological deficit. Analysis of a subset of the experimental groups revealed weight gain without statistical difference during exposure to air, NO at 20 ppm and NO at 80 ppm.

Figure 4:
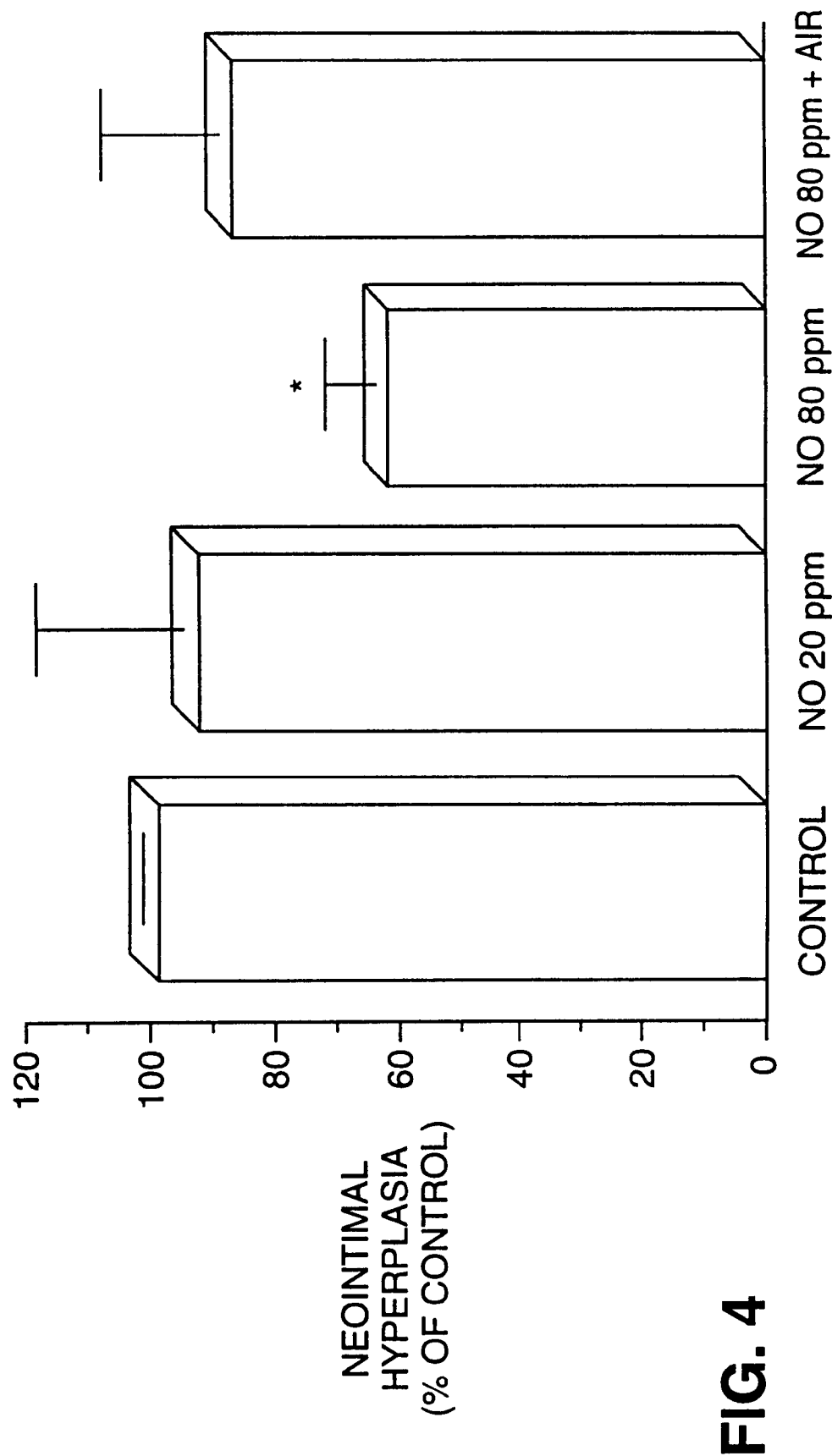
FIG. 4 is a graph comparing the intima/media ratio in control rats; rats exposed for two weeks to 20 ppm NO; rats exposed for two weeks to 80 ppm NO; and rats exposed for one week to 80 ppm NO, followed by one week of breathing air. The asterisk indicates value significantly differs from baseline ($p<0.05$).

In the first series of experiments, the rats undergoing carotid balloon injury were exposed to either ambient air (n=12) or 80 ppm NO (n=13) in air, throughout the duration of the study. The animals were sacrificed 14 days after injury for morphometric analysis of the injured carotid artery. Examination by light microscopy revealed that three rats from the air (control) group and one rat from the NO-treated group had thrombotic occlusion of the lumen of the injured carotid. These animals were excluded from further analysis. As expected, blood vessels from both groups exhibited a loss of endothelium and the development of neointimal hyperplasia. Examination by light microscopy did not reveal a qualitative difference in the cellular morphology of the neointima (data not shown). Quantitive analysis, however, revealed that the 80 ppm inhaled NO treatment resulted in a 38% inhibition of neointimal hyperplasia, i.e., intima/media ratio of 0.932+/−0.13 in 80 ppm animals, compared to 1.512+/−0.147 in 0 ppm NO (control) animals (P=0.008) (FIG. 4).

In the next series of experiments, the effect of a one week exposure to NO was tested. The experimental group (n=7) was exposed to 80 ppm NO for seven days and then transferred to air for an additional seven days, prior to sacrifice. The control group (n=5) was exposed to air for the entire 14 day period. There was no qualitative morphologic difference between the groups. In addition, quantitive analysis of the intima/media ratio revealed no significant difference in neointimal hyperplasia between the two groups, i.e., 1.059+/−0.239 in NO-treated animals, compared to 1.217+/−0.309 in controls (P=not significant) (FIG. 4).

In a third series of experiments, a lower inhaled dose of NO was studied: the rats breathed either 20 ppm NO (n=8) or air (n=8). Again, no quantitative or qualitive difference in the degree of neointimal hyperplasia could be found between the 2 groups, i.e., intima/media ratio of 0.917+/−0.233 for 20 ppm NO-treated animals, compared to 0.985+/−0.149 for air-breathing controls (P=not significant) (FIG. 4).

The above results demonstrate that inhalation of 80 ppm NO, over a two-week period, significantly inhibits neointimal hyperplasia following balloon-induced injury to carotid arteries, in a rodent model.

Other embodiments of the invention are within the following claims.

What is claimed is:

1. A method for treating, inhibiting or preventing vascular thrombosis in a mammal, which method comprises the steps of:
   (a) identifying a mammal that has an existing thrombosis or is at risk for developing a thrombosis; and
   (b) causing said mammal to inhale a therapeutically effective concentration of gaseous nitric oxide (NO); and
   (c) administering to said mammal a therapeutically effective amount of a phosphodiesterase inhibitor without inducing acute systemic hypotension.

2. The method of claim 1, wherein said mammal is a human.

3. The method of claim 1, wherein said thrombosis is an arterial thrombosis.

4. The method of claim 1, wherein said thrombosis is a venous thrombosis.

5. The method of claim 1, wherein said thrombosis is not a pulmonary thrombosis.

6. The method of claim 1, wherein said mammal has or is at risk of developing an acute ischemic coronary syndrome.

7. The method of claim 6, wherein said acute ischemic coronary syndrome is selected from the group consisting of myocardial infarction, unstable angina pectoris, thrombosis after coronary revascularization, and reocclusion after coronary thrombolysis.

8. The method of claim 6, wherein said acute ischemic coronary syndrome is associated with an artery-occluding disease.

9. The method of claim 6, wherein the acute ischemic coronary syndrome is associated with a vascular interventional procedure.

10. The method of claim 9, wherein said vascular interventional procedure is selected from the group consisting of angioplasty, coronary artery surgery and coronary artery stents.

11. The method of claim 10, wherein the angioplasty is percutaneous transluminal coronary angioplasty (PTCA).

12. The method of claim 1, wherein said NO is inhaled in a predetermined concentration range.

13. The method of claim 12, wherein said concentration range is 0.1 ppm to 300 ppm.

14. The method of claim 12, wherein said concentration range is 1.0 ppm to 200 ppm.

15. The method of claim 12, wherein said concentration range is 20 ppm to 100 ppm.

16. The method of claim 1, wherein said gaseous NO is inhaled as a mixture comprising NO, oxygen ($O_2$), and nitrogen ($N_2$) gases.

17. The method of claim 16, wherein said mixture comprises between 20% and 99% $O_2$ gas, by volume.

18. The method of claim 16, wherein said $O_2$ is mixed with said NO immediately before said mixture is inhaled by the mammal.

19. The method of claim 1, wherein said phosphodiesterase inhibitor is selected from the group consisting of 2-o-propoxyphenyl-8-azapurin-6-one, dipyridamole and theophyline.

20. The method of claim 1, further comprising administering to said mammal, in conjunction with NO inhalation, a therapeutically effective amount of a second antithrombotic agent.

21. The method of claim 20, wherein said second antithrombotic agent is selected from the group consisting of aspirin, ticlopidine, streptokinase, urokinase, tissue plasminogen activator (t-PA), met-t-PA, FE1X, heparin, hirudin and a hirudin analog.

22. The method of claim 1, wherein said gaseous NO is inhaled in the absence of tobacco smoke.

23. The method of claim 1, wherein said NO is inhaled continuously for an extended period.

24. The method of claim 1, wherein said NO is inhaled intermittently for an extended period.

* * * * *